United States Patent [19]
Amato

[11] Patent Number: 5,520,624
[45] Date of Patent: May 28, 1996

[54] BACK SUPPORT

[76] Inventor: William J. Amato, 700 Sunset Dr., Lakewood, Colo. 80228

[21] Appl. No.: 371,365

[22] Filed: Jan. 11, 1995

[51] Int. Cl.$^6$ ........................................... A61F 5/02
[52] U.S. Cl. ..................... 602/19; 5/633; 128/845
[58] Field of Search ..................... 128/845; 5/432, 5/436, 622, 624, 633, 636, 637; 602/19; 297/284.4, 391, 452.29, 452.3, 452.31

[56] References Cited

U.S. PATENT DOCUMENTS

| | | |
|---|---|---|
| D. 333,939 | 3/1993 | Gates . |
| 4,835,801 | 6/1989 | Walpin et al. ........................... 5/652 |
| 4,905,993 | 3/1990 | Barone ................................... 602/19 X |
| 4,991,573 | 2/1991 | Miller ..................................... 602/19 |
| 5,007,633 | 4/1991 | Lemire ................................... 602/19 X |
| 5,279,310 | 1/1994 | Hsien ..................................... 5/636 X |

Primary Examiner—Richard J. Apley
Assistant Examiner—Kim M. Lee

[57] ABSTRACT

A back support for placement on a back of a person. The back support comprises a concavity having opposing lateral slopes and formed by a flexible structure having a thickness and a longitudinal central site disposed substantially equidistant between the opposing lateral slopes. A protuberance having a thickness extends into the concavity, and preferably is substantially tubular in shape and disposed substantially equidistantly between the opposing lateral slopes of the concavity along the longitudinal central site. The thickness of the protuberance is greater than the thickness of the flexible structure forming the concavity. A lip surrounds the concavity to thereby aid in achieving a suctorial characteristic for the back support whereby the concavity in concert with the lip will function in substantially the same manner as a suction cup. The back support is preferably constructed of a single piece of material wherein the protuberance is a thickened region of the flexible structure forming the concavity. Construction can be of a material having an inherently-tacky surface to thereby enhance the clinging action of the back support to the skin of a user.

11 Claims, 1 Drawing Sheet

BACK SUPPORT

BACKGROUND OF THE INVENTION

This invention relates in general to a back support for a person, and in particular to a back support substantially retained by suction, with or without a tacky surface characteristic, in spinal-column alignment on the skin of the back of a person without straps or additional retention devices.

Back pain and related discomforts such as leg and hip pain are prevalent among many individuals as they engage in routine daily activities such as sitting for a period of time, walking, lifting objects, and the like, or as they perform non-routine tasks such as participating in new sports activities that exert unusual demands on their backs. One apparent cause for back and related discomfort appears to be a malfunction of the vertebrae in the lumbar region of the spinal column. These lumbar vertebrae are situated in the area commonly referred to as the "small of the back," an area at and below the waist of an individual. In particular, the lumbar vertebrae become misaligned and create a pressure on the nerves leading from the spinal cord in the lumbar region. This pressure, as well as strain on nearby muscles, can cause back pain, leg pain, hip pain, and the like.

Numerous procedures and devices have been introduced over the years to reduce or eliminate these discomforts. Physicians have performed surgery, while chiropractors and therapists have performed manipulations to correct the affliction. Various belts, corsets, etc., which generally require accompanying straps or other retainer means, have been made available in respective attempts to solve and correct the distress. Swanson, in U.S. Pat. No. Des. 253,982, shows an apparent convex-surface pad for assumed placement against the spinal column. A flat side opposite the convex surface apparently has retainer means for retention of the pad on clothing covering the pad. Another device that preceded the present invention was a laminated, two-piece back support wherein the surface designated to be against the skin in alignment with the spinal column behaved as an aggressive adhesive and had no defined concavity to give it suctorial characteristics. The device faltered in long-term practical usefulness in that its aggressive adhesiveness could tear skin, its lamination could fail and its two pieces would separate to thereby eliminate support action, and its material could decompose and become a health hazard.

In view of the pronounced scope of back and related pain experienced by many people, it is apparent that a need is present for a back support that is effective in alleviating this pain and is easy and convenient to use. It is therefore a primary object of the present invention to provide a back support having a suctorial characteristic created by a defined concavity which results in suction-clinging to the skin of a user without straps, belts, or the like.

Yet another object of the present invention is to provide a back support wherein a protuberance extending into the defined concavity of the support can be positioned in substantial alignment with the spinal column of the user to thereby function in maintaining alignment of the vertebrae affected by such alignment.

Still another object of the present invention is to provide a back support constructed of one-piece flexible material.

These and other objects of the present invention will become apparent throughout the description of the invention which now follows.

SUMMARY OF THE INVENTION

The present invention is a back support for placement on a back of a person. The back support comprises a concavity having opposing lateral slopes and formed by a flexible structure having a thickness and a longitudinal central site disposed substantially equidistant between the opposing lateral slopes. A protuberance having a thickness extends into the concavity, and preferably is substantially tubular in shape and disposed substantially equidistantly between the opposing lateral slopes of the concavity along the longitudinal central site. The thickness of the protuberance is greater than the thickness of the flexible structure forming the concavity. A lip surrounds the concavity to thereby aid in achieving a suctorial characteristic for the back support whereby the concavity in concert with the lip will function in substantially the same manner as a suction cup. The back support is preferably constructed of a single piece of material wherein the protuberance is a thickened region of the flexible structure forming the concavity. Construction can be of a material having an inherently-tacky surface to thereby enhance the clinging action of the back support to the skin of a user.

BRIEF DESCRIPTION OF THE DRAWINGS

An illustrative and presently preferred embodiment of the invention is shown in the accompanying drawings in which.

DETAILED DESCRIPTION OF THE PREFERRED EMBODIMENT

Figure 1:
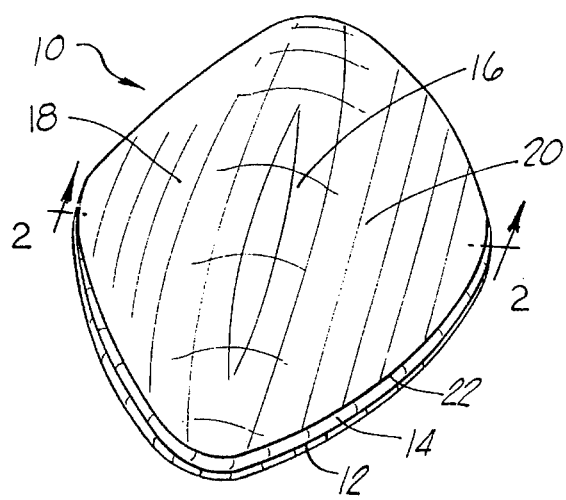
FIG. 1 is a perspective view of a back support of the prior art.
Figure 2:
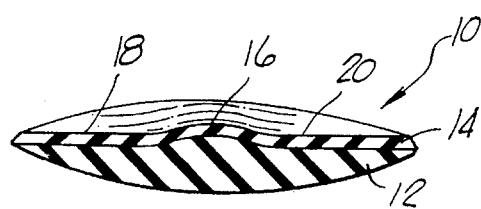
FIG. 2 is a cross section view along line 2—2 of the prior art back support of FIG. 1.
Figure 3:
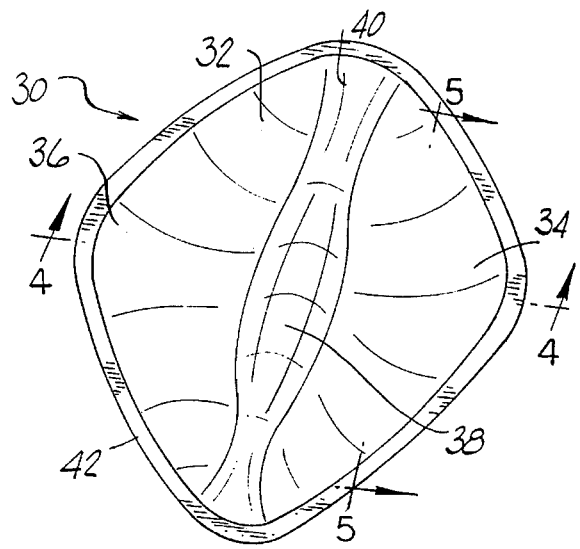
FIG. 3 is a perspective view of a back support according to the present invention.
Figure 4:
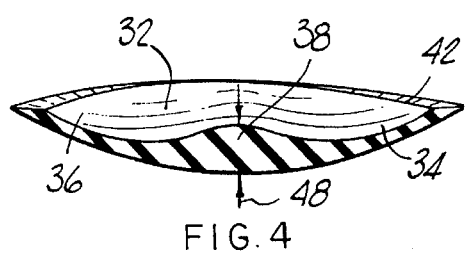
FIG. 4 is a cross section view along line 4—4 of FIG. 3.
Figure 5:
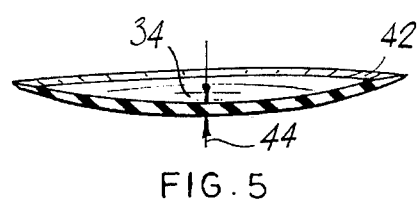
FIG. 5 is a cross section view along line 5—5 of FIG. 3.
Figure 6:
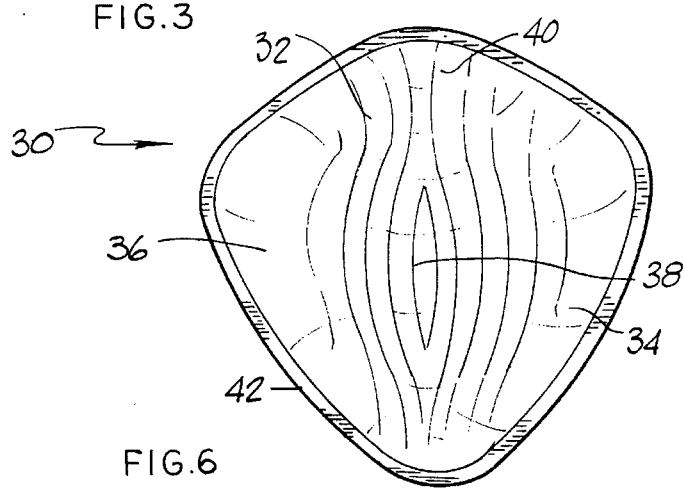
FIG. 6 is a front elevation view of the back support of FIG. 3.

Referring to FIGS. 1 and 2, a prior art back support 10 is shown. The back support 10 is the two-piece back support referred to in the Background of the Invention section above, and is constructed of two pieces of laminated material 12, 14. The piece 14 is that which would contact the skin of a user, with the hump 16 placed in alignment with a spinal column of the user. The respective surfaces 18, 20 lateral to the hump 16 are substantially flat and do not form a concavity, while the border 22 around the back support 10 has no lip. As earlier noted, the material forming the prior art back support 10, as defined by the surfaces 18, 20, behaved as an aggressive adhesive to thereby retain the device on the back of a user. The back support 10 had no defined concavity or surrounding lip, and therefore had no suctorial characteristics for retention on the skin of a user.

FIGS. 3 through 7 illustrate a back support 30 in accord with the present invention. As shown in FIGS. 3–6, the back support 30 has a concavity 32 having opposing lateral slopes 34, 36 and a protuberance 38 having a substantially tubular shape extending therein. The protuberance 38 is disposed along a longitudinal central site 40 disposed substantially equidistant between the opposing lateral slopes 34, 36. A lip 42 surrounds the concavity 32. The concavity 32 is formed by a flexible structure having a thickness 44. As used herein, "flexible" means movable with the back of a user when the back support 30 is in contact with the back and the user bends or otherwise flexes his or her back. The preferred embodiment is constructed of a composition of matter identified as Compound No. RD-5232, a rubber compound mixture manufactured by Colonial Rubber Works, Inc., Dyersburg, Tenn. The Compound has a 25 Shore A hardness, and is tacky. When such a tacky surface is included as part of the present invention, the degree of adhesiveness of the surface must be such that the back support 30 will not tear tissue with which it is in contact when the back support 30 is removed from the skin of a user. Thus, "tacky" as used herein is defined as being an adhesive magnitude which is non-injurious upon removal from human skin having normal characteristics. While the identified composition is preferred, it is to be understood that any material that accomplishes the utility of the invention can be employed in its construction.

While more than one piece of a material can be utilized in constructing the invention, it is preferred that the entire back support 30 be constructed of a single piece of material as shown in the drawing figures. As such, the protuberance 38, which has a thickness 48 greater than the thickness 44 of the flexible structure forming the concavity 32, is preferably a thickened region of the flexible structure forming the concavity 32, thereby accomplishing one-piece construction. Of course, the protuberance 38 could be constructed of a separate piece of material and thereafter secured within the concavity 32. The thickness of the protuberance 38 in the preferred embodiment is between about 0.60 and 0.65 inch.

Figure 7:
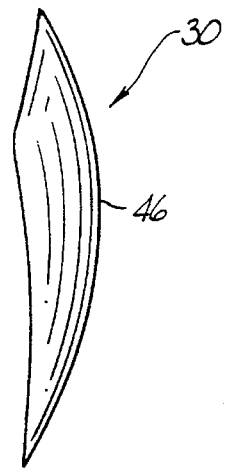
FIG. 7 is a side elevation view of the back support of FIG. 3.

As would be apparent to a skilled artisan, the back support 30 can be manufactured through utilization of a mold process as known in the art. FIG. 7 shows the shape of the back side 46 of the back support 30 as being curved convexly in complimentary accord with the concave shape of the concavity 32 formed by the flexible structure as earlier described. This convex shape of the back side 46 also conforms with the posture of a user bending forward. While the back support 30 is flexible, it has memory such that it returns to its at-rest shape when not being flexed. The flexibility of the back support 30 permits it to advantageously conform to the natural curvature of the spinal column of the user, irrespective of whether such curve is large or small.

In use, the back support 30 is positioned directly against the skin of the user, with the protuberance 38 substantially in alignment with the lumbar region (the "small of the back") of the spinal column. The concavity 32 and the lip 42 work in concert to provide a suctorial characteristic to the back support 30, with the back support 30 clinging to the skin of the user in a similar manner as a conventional suction cup clings to a surface. Thus, the back support 30 requires no belts, straps or other attachment devices to keep it in place, resists slipping and shifting out of place, and is non-restrictive with respect to movement of the user. The protuberance 32 supports and keeps in substantial alignment the vertebrae of the lumbar region of the spinal column to thereby relieve pressure on nerves emanating therefrom and accomplish relief from pain and discomfort of the back and of the body portions served by the nerves affected.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

I claim:

1. A back support adapted for placement on a back of a person having a spinal column including vertebrae of a lumbar region, the back support comprising:

(a) a flexible member having suctorial characteristics created by a defined concavity, a thickness and an outer periphery, said concavity having opposing lateral arcuate slopes and a longitudinal central site substantially equidistant between said opposing lateral slopes;

(b) a protuberance positioned at said longitudinal central site, said protuberance having a thickness and extending inwardly into said concavity, with the thickness of said protuberance being greater than the thickness of said flexible member; and (c) a lip substantially surrounding said outer periphery of said flexible member and having a substantially flat surface, whereby when worn by a person, said concavity results in suction-clinging to the skin of a patient and allows said protuberance to support and keep in substantial alignment the vertebrae of the lumbar region of the spinal column.

2. A back support as claimed in claim 1 wherein the protuberance has a substantially tubular shape and is disposed substantially equidistantly between the opposing lateral slopes of the concavity along the longitudinal central site.

3. A back support as claimed in claim 2 wherein the back support is constructed of a single piece of a material.

4. A back support as claimed in claim 3 wherein the material has about a 25 Shore A hardness.

5. A back support as claimed in claim 4 wherein the material is tacky.

6. A back support as claimed in claim 3 wherein the material is tacky.

7. A back support as claimed in claim 1 wherein the thickness of the protuberance is between about 0.60 and about 0.65 inch.

8. A back support as claimed in claim 2 wherein the thickness of the protuberance is between about 0.60 and about 0.65 inch.

9. A back support as claimed in claim 3 wherein the thickness of the protuberance is between about 0.60 and about 0.65 inch.

10. A back support as claimed in claim 4 wherein the thickness of the protuberance is between about 0.60 and about 0.65 inch.

11. A back support as claimed in claim 6 wherein the thickness of the protuberance is between about 0.60 and about 0.65 inch.

* * * * *